(12) United States Patent
Hagen et al.

(10) Patent No.: US 6,265,528 B1
(45) Date of Patent: Jul. 24, 2001

(54) PREPARATION OF POLYOXYMETHYLENE DIMETHYL ETHERS BY ACID-ACTIVATED CATALYTIC CONVERSION OF METHANOL WITH FORMALDEHYDE FORMED BY OXY-DEHYDROGENATION OF DIMETHYL ETHER

(75) Inventors: Gary P. Hagen, West Chicago; Michael J. Spangler, Sandwich, both of IL (US)

(73) Assignee: BP Corporation North America Inc., Chicago, IL (US)

( * ) Notice: Subject to any disclaimer, the term of this patent is extended or adjusted under 35 U.S.C. 154(b) by 0 days.

(21) Appl. No.: 09/190,699

(22) Filed: Nov. 12, 1998

(51) Int. Cl.$^7$ .............. C08G 6/00; C07C 43/04
(52) U.S. Cl. ............ 528/230; 528/232; 528/233; 528/240; 528/242; 528/244; 528/425; 568/470; 568/472; 568/473; 568/606; 568/613
(58) Field of Search .................... 528/232, 230, 528/242, 425, 233, 240, 244; 568/606, 613, 470, 472, 473

(56) References Cited

U.S. PATENT DOCUMENTS

| | | |
|---|---|---|
| 2,449,469 | 9/1948 | Gresham et al. . |
| 2,663,742 | 12/1953 | Frevel et al. . |
| 2,882,243 | 4/1959 | Milton . |
| 2,882,244 | 4/1959 | Milton .................. 252/455 |
| 3,130,007 | 4/1964 | Breck ..................... 23/113 |
| 3,702,886 | 11/1972 | Argauer et al. ............ 423/328 |
| 3,709,979 | 1/1973 | Chu ....................... 423/328 |
| 3,832,449 | 8/1974 | Rosinski et al. ............ 423/328 |
| 4,215,011 | 7/1980 | Smith .................... 252/426 |
| 4,341,069 | 7/1982 | Bell et al. ............... 60/39.02 |
| 4,359,587 | 11/1982 | Abdurakhmanov et al. ....... 568/402 |
| 4,443,559 | 4/1984 | Smith, Jr. ................. 502/527 |
| 4,474,996 | 10/1984 | Carcia et al. .............. 568/473 |
| 4,521,618 | 6/1985 | Arntz et al. ............... 562/535 |
| 4,786,743 | 11/1988 | Bongaarts et al. ........... 549/348 |
| 4,967,014 | 10/1990 | Masamoto et al. ........... 568/458 |
| 5,102,838 | 4/1992 | Beck et al. ................ 502/60 |
| 5,113,015 | 5/1992 | Plamer et al. .............. 562/608 |
| 5,401,884 | 3/1995 | Diercks et al. ............. 568/487 |
| 5,746,785 | 5/1998 | Moulton et al. ............. 44/443 |

FOREIGN PATENT DOCUMENTS

| | | |
|---|---|---|
| 25207 | 9/1984 | (AU) . |
| 245868 | 5/1987 | (GB) . |
| 688041 | 4/1997 | (GB) . |

OTHER PUBLICATIONS

Derwent Abstract ACC_NO1983–58328K, 1983.*

* cited by examiner

Primary Examiner—Jeffrey Mullis
(74) Attorney, Agent, or Firm—Ekkehard Schoettle (57) ABSTRACT

A particularly useful process which includes the steps of providing a feedstream comprising a soluble condensation promoting component capable of activating a heterogeneous acidic catalyst and a source of formaldehyde formed by conversion of dimethyl ether in the presence of a catalyst comprising silver as an essential catalyst component; and heating the feedstream with the heterogeneous acidic catalyst in a catalytic distillation column to convert methanol and formaldehyde present to methylal and higher polyoxymethylene dimethyl ethers and to separate the methylal from the higher polyoxymethylene dimethyl ethers is disclosed. Advantageously, methylal and higher polyoxymethylene dimethyl ethers are formed and separated in a catalytic distillation column. By including in the column an anion exchange resin, an essentially acid-free product is obtained which can be used directly as a blending component, or fractionated, as by further distillation, to provide more suitable components for blending into diesel fuel.

18 Claims, 1 Drawing Sheet

PREPARATION OF POLYOXYMETHYLENE DIMETHYL ETHERS BY ACID-ACTIVATED CATALYTIC CONVERSION OF METHANOL WITH FORMALDEHYDE FORMED BY OXY-DEHYDROGENATION OF DIMETHYL ETHER

TECHNICAL FIELD

The present invention relates to production of organic compounds, particularly polyoxymethylene dimethyl ethers, which are suitable components for blending into fuel having improved qualities for use in diesel engines. More specifically, it relates to providing a feedstream comprising methanol, formaldehyde and a soluble condensation promoting component capable of activating a heterogeneous acidic catalyst, and heating this feedstream with the heterogeneous acidic catalyst in a catalytic distillation column to convert methanol and formaldehyde present to methylal and higher polyoxymethylene dimethyl ethers and separate the methylal from the higher polyoxymethylene dimethyl ethers. Advantageously, the catalytic distillation column has a section containing an anion exchange resin whereby an essentially acid-free product is obtained which can be used directly as a blending component, or fractionated, as by further distillation, to provide more suitable components for blending into diesel fuel.

This integrated process also provides its own source of formaldehyde which is an un-purified liquid stream derived from a mixture formed by oxidative dehydrogenation (oxy-dehydrogenation) of dimethyl ether using a catalyst based silver as an essential catalyst.

BACKGROUND OF THE INVENTION

Conversion of low molecular weight alkanes such as methane to synthetic fuels or chemicals has received increasing attention because low molecular weight alkanes are generally available from secure and reliable sources. For example, natural gas wells and oil wells currently produce vast quantities of methane. Reported methods for converting low molecular weight alkanes to more easily transportable liquid fuels and chemical feedstocks can be conveniently categorized as direct oxidative routes and/or as indirect syngas routes. Direct oxidative routes convert lower alkanes to products such as methanol, gasoline, and relatively higher molecular weight alkanes. In contrast, indirect syngas routes typically involve production of synthesis gas as an intermediate product.

Routes are known for converting methane to dimethyl ether. For example, methane is steam reformed to produce synthesis gas. Thereafter, dimethyl ether and methanol can be manufactured simultaneously from the synthesis gas, as described in U.S. Pat. No. 4,341,069 issued to Bell et al. They recommend a dimethyl ether synthesis catalyst having copper, zinc, and chromium co-precipitated on a gamma-alumina base. Alternatively, methane is converted to methanol, and dimethyl ether is subsequently manufactured from methanol by passing a mixed vapor containing methanol and water over an alumina catalyst, as described in an article by Hutchings in New Scientist Jul. 3, 1986) 35.

Formaldehyde is a very important intermediate compound in the chemical industry. The extreme reactivity of the formaldehyde carbonyl group and the nature of the molecule as a basic building block has made formaldehyde an important feedstock for a wide variety of industrially important chemical compounds. Historically, formaldehyde has found its largest volume of application in the manufacture of phenol-formaldehyde resins, urea-formaldehyde resins and other polymers. Pure formaldehyde is quite uncommon since it polymerizes readily. It was usually obtained as an aqueous solution such as formalin, which contains only about 40 percent formaldehyde. However, more recently, formaldehyde is usually transported as an item of commerce in concentrations of 37 to 50 percent by weight. A solid source of formaldehyde called paraformaldehyde is also commercially available.

Because of the reactivity of formaldehyde, its handling and separation require special attention. It is a gas above $-19°$ C. and is flammable or explosive in air at concentrations of about 7 to about 12 mol percent. Formaldehyde polymerizes with itself at temperatures below $100°$ C. and more rapidly when water vapor or impurities are present. Since formaldehyde is usually transported in aqueous solutions of 50 percent by weight or lower concentration, producers have tended to locate close to markets and to ship the methanol raw material, which has a smaller volume.

It is known that some reactions may be carried out by means of catalytic distillation. In catalytic distillation, reaction and separation are carried out simultaneously in a distillation column with internal and/or external stages of contact with catalyst.

In U.S. Pat. No. 4,215,011, Smith, Jr. discloses a method for the separation of an isoolefin, preferably having four to six carbon atoms, from streams containing mixtures thereof with the corresponding normal olefin, wherein the mixture is fed into a reaction-distillation column containing a fixed-bed, acidic cation exchange resin and contacted with the acidic cation exchange resin to react the isoolefin with itself to form a dimer and the dimer is separated from the normal olefin, the particulate catalytic material, i.e., the acidic cation exchange resin, being contained in a plurality of closed cloth pockets, which pockets are arranged and supported in the column by wire mesh.

In U.S. Pat. No. 4,443,559, Smith, Jr. discloses a catalytic distillation structure which comprises a catalyst component associated intimately with or surrounded by a resilient component, which component is comprised of at least 70 vol. percent open space for providing a matrix of substantially open space. Examples of such resilient component are open-mesh, knitted, stainless wire (demister wire or an expanded aluminum); open-mesh, knitted, polymeric filaments of nylon, Teflon, etc.; and highly-open structure foamed material (reticulated polyurethane).

In U.S. Pat. No. 5,113,015, David A. Palmer, K. D. Hansen and K. A. Fjare disclose to a process for recovering acetic acid from methyl acetate wherein the methyl acetate is hydrolyzed to methanol and acetic acid via catalytic distillation.

In German Democratic Republic DD 245 868 A1 published May 20, 1987 in the text submitted by the applicant, preparation of methylal is carried out by reaction of methanol with trioxane, formalin or paraformaldehyde in the presence of a specific zeolite. Autoclave reactions of 1 to 8 hours are described using a zeolite of the "LZ40 type" with a ratio of silicon dioxide to alumina ratio of 78 at temperatures from 493 to 543 K. Methylal content of the product as high as 99.8 percent (without methanol) is reported for trioxane at 523 K for 3 hours. Reaction pressures did not exceed 5 MPa in the autoclave. Neither conversions nor selectivity are reported.

In U.S. Pat. No. 4,967,014, Junzo Masamoto, Junzo Ohtake and Mamoru Kawamura describe a process for formaldehyde production by reacting methanol with formaldehyde to form methylal, $CH_3OCH_2OCH_3$, and then oxidizing the resulting methylal to obtain formaldehyde. In the methylal formation step, a solution containing methanol, formaldehyde and water was brought into solid-liquid contact with a solid acid catalyst, and a methylal-rich component was recovered as a distillate. This process employs reactive distillation performed using a distillation column and multireaction units. The middle portion of the distillation column was furnished with stages from which the liquid components were withdrawn and pumped to the reactor units, which contained solid acid catalyst. The reactive solutions containing the resulting methylal were fed to the distillation column, where methylal was distilled as the overhead product.

Polyoxymethylene dimethyl ethers are the best known members of the dialkyl ether polymers of formaldehyde. While diethyl and dipropyl polyoxymethylene ethers have been prepared, major attention has been given to the dimethyl ether polymers. Polyoxymethylene dimethyl ethers make up a homologous series of polyoxymethylene glycol derivatives having the structure represented by use of the type formula indicated below:

$$CH_3O(CH_2O)_nCH_3$$

Chemically, they are acetals closely related to methylal, $CH_3OCH_2CH_3$, which may be regarded as the parent member of the group in which n of the type formula equals 1. They are synthesized by the action of methanol on aqueous formaldehyde or polyoxymethylene glycols in the presence of an acidic catalyst just as methylal is produced. On hydrolysis they are converted to formaldehyde and methanol. Like other acetals, they possess a high degree of chemical stability. They are not readily hydrolyzed under neutral or alkaline conditions, but are attacked by even relatively dilute acids. They are more stable than the polyoxymethylene diacetates.

Due to the relatively small differences in the physical properties (melting points, boiling points, and solubility) of adjacent members in this series, individual homologs are not readily separated. However, fractions having various average molecular weight values have been isolated. The normal boiling point temperature of a fraction having average n of 2 in the type formula is reported as 91° to 93° C. Boiling points at atmospheric pressure calculated from partial pressure equations range from 105.0° C. for n of 2, to 242.3° C. for n of 5. (Walker, Joseph Frederic, "Formaldehyde", Robert E. Krieger Publishing Co., issued as No. 159 of American Chemical Society Monograph series (1975), pages 167–169)

Polyoxymethylene dimethyl ethers are prepared in laboratory scale by heating polyoxymethylene glycols or paraformaldehyde with methanol in the presence of a trace of sulfuric or hydrochloric acid in a sealed tube for 15 hours at 150° C., or for a shorter time (12 hours) at 165° to 180° C. Considerable pressure is caused by decomposition reactions, which produce carbon oxides, and by formation of some dimethyl ether. The average molecular weight of the ether products increases with the ratio of paraformaldehyde or polyoxymethylene to methanol in the charge. A high polymer is obtained with a 6 to 1 ratio of formaldehyde (as polymer) to methanol. In these polymers, the n value of the type formula $CH_3O(CH_2O)_nCH_3$ is greater than 100, generally in the range of 300 to 500. The products are purified by washing with sodium sulfite solution, which does not dissolve the true dimethyl ethers, and may then be fractionated by fractional crystallization from various solvents.

U.S. Pat. No. 2,449,469 in the names of W. F. Gresham and R. E. Brooks reported obtaining good yields of polyoxymethylene dimethyl ethers containing 2 to 4 formaldehyde units per molecule. This procedure is carried out by heating methylal with paraformaldehyde or concentrated formaldehyde solutions in the presence of sulfuric acid.

In the past, various molecular sieve compositions, natural and synthetic, have been found to be useful for a number of hydrocarbon conversion reactions. Among these are alkylation, aromatization, dehydrogenation and isomerization. Among the sieves which have been used are Type A, X, Y and those of the MFI crystal structure as shown in "Atlas of Zeolite Structure Types," Second Revised Edition, 1987, published on behalf of the Structure Commission of the International Zeolite Associates and incorporated by reference herein. Representative of the last group are ZSM-5 and AMS borosilicate molecular sieves.

Prior art developments have resulted in the formation of many synthetic crystalline materials. Crystalline aluminosilicates are the most prevalent and, as described in the patent literature and in the published journals, are designated by letters or other convenient symbols. Exemplary of these materials are Zeolite A (Milton, in U.S. Pat. No. 2,882,243), Zeolite X (Milton, in U.S. Pat. No. 2,882,244), Zeolite Y (Breck, in U.S. Pat. No. 3,130,007), Zeolite ZSM-5 (Argauer, et al., in U.S. Pat. No. 3,702,886), Zeolite ZSM-11 (Chu, in U.S. Pat. No. 3,709,979), Zeolite ZSM-12 (Rosinski, et al., in U.S. Pat. No. 3,832,449), and others.

It is well known that internal combustion engines have revolutionized transportation following their invention during the last decades of the 19th century. While others, including Benz and Gottleib Wilhelm Daimler, invented and developed engines using electric ignition of fuel such as gasoline, Rudolf C. K. Diesel invented and built the engine named for him which employs compression for autoignition of the fuel in order to utilize low-cost organic fuels. Development of improved diesel engines for use in automobiles has proceeded hand-in-hand with improvements in diesel fuel compositions, which today are typically derived from petroleum. Modern high performance diesel engines demand ever more advanced specification of fuel compositions, but cost remains an important consideration.

Even in newer, high performance diesel engines combustion of conventional fuel produces smoke in the exhaust. Oxygenated compounds and compounds containing few or no carbon-to-carbon chemical bonds, such as methanol and dimethyl ether, are known to reduce smoke and engine exhaust emissions. However, most such compounds have high vapor pressure and/or are nearly insoluble in diesel fuel, and they have poor ignition quality, as indicated by their cetane numbers. Furthermore, other methods of improving diesel fuels by chemical hydrogenation to reduce their sulfur and aromatics contents, also causes a reduction in fuel lubricity. Diesel fuels of low lubricity may cause excessive wear of fuel injectors and other moving parts which come in contact with the fuel under high pressures.

Recently, U.S. Pat. No. 5,746,785 in the names of David S. Moulton and David W. Naegeli reported blending a mixture of alkoxy-terminated poly-oxymethylenes, having a varied mixture of molecular weights, with diesel fuel to form an improved fuel for autoignition engines. Two mixtures were produced by reacting paraformaldehyde with (i) methanol or (ii) methylal in a closed system for up to 7 hours and at a temperatures of 150° to 240° C. and pressures of 300 psi to 1,000 psi to form a product containing methoxy-terminated poly-oxymethylenes having a molecular weight of from about 80 to about 350 (polyoxymethylene dimethyl ethers). More specifically, a 1.6 liter cylindrical reactor was loaded with a mixture of methanol and paraformaldehyde, in molar ratio of about 1 mole methanol to 3 moles paraformaldehyde, and in a second preparation, methylal (dimethoxymethane) and paraformaldehyde were combined in a molar ratio of about 1 mole methylal to about 5 moles paraformaldehyde. In the second procedure, a small amount of formic acid, about 0.1 percent by weight of the total reactants, was added as a catalyst. The same temperatures, pressures and reaction times are maintained as in the first. Disadvantages of these products include the presence of formic acid and thermal instability of methoxy-terminated poly-oxymethylenes under ambient pressure and acidic conditions.

There is, therefore, a present need for catalytic processes to prepare oxygenated organic compounds, particularly polyoxymethylene dimethyl ethers, which do not have the above disadvantages. An improved process should be carried out advantageously in the liquid phase using a suitable condensation-promoting catalyst system, preferably a molecular sieve based catalyst which provides improved conversion and yield. Such an improved process which converts lower value compounds to higher polyoxymethylene dimethyl ethers would be particularly advantageous. Dimethyl ether is, for example, less expensive to produce than methanol on a methanol equivalent basis, and its condensation to polyoxymethylene dimethyl ethers does not produce water as a co-product.

The base diesel fuel, when blended with such mixtures in a volume ratio of from about 2 to about 5 parts diesel fuel to 1 part of the total mixture, is said to provide a higher quality fuel having significantly improved lubricity and reduced smoke formation without degradation of the cetane number or smoke formation characteristics as compared to the base diesel fuel.

This invention is directed to overcoming the problems set forth above in order to provide Diesel fuel having improved qualities. It is desirable to have a method of producing a high quality diesel fuel that has better fuel lubricity than conventional low-sulfur, low-aromatics diesel fuels, yet has comparable ignition quality and smoke generation characteristics. It is also desirable to have a method of producing such fuel which contains an additional blended component that is soluble in diesel fuel and has no carbon-to-carbon bonds. Furthermore, it is desirable to have such a fuel wherein the concentration of gums and other undesirable products is reduced.

SUMMARY OF THE INVENTION

Economical processes are disclosed for production of a mixture of oxygenated organic compounds which are suitable components for blending into fuel having improved qualities for use in compression ignition internal combustion engines (diesel engines).

According to the present invention, there is now provided a continuous process for catalytic production of oxygenated organic compounds, particularly polyoxymethylene dimethyl ethers. More specifically, continuous processes of this invention comprise providing a feedstream comprising methanol, formaldehyde and a soluble condensation promoting component capable of activating a heterogeneous acidic catalyst, and heating the feedstream with the heterogeneous acidic catalyst under conditions of reaction sufficient to form an effluent of condensation comprising water, methanol and one or more polyoxymethylene dimethyl ethers having a structure represented by the type formula in which formula n is a number from 1 to about 10. Advantageously, at least a liquid of the effluent containing polyoxymethylene dimethyl ethers is contacted with an anion-exchange resin to form an essentially acid-free mixture.

Suitable soluble condensation promoting components capable of activating the heterogeneous acidic catalyst comprises at least one member of the group consisting of low boiling, monobasic organic acids, preferable the group consists of formic acid and acetic acid. More preferable soluble condensation promoting component capable of activating the heterogeneous acidic catalyst comprises at least formic acid.

Preferably, the heating of the feedstream with the acidic catalyst is carried out at in at least one catalytic distillation column having internal and/or external stages of contact with the acidic catalyst and internal zones to separate methylal from higher polyoxymethylene dimethyl ethers. In a preferred embodiment of the invention at least a liquid portion of the effluent containing polyoxymethylene dimethyl ethers is contacted with an anion exchange resin disposed within a section of the distillation column below the stages of contact with the acidic catalyst to form an essentially acid-free mixture. Advantageously, the essentially acid-free mixture of polyoxymethylene dimethyl ethers is fractionated within a section of the distillation column below the stages of contact with the acidic catalyst to provide an aqueous side-stream which is withdrawn from the distillation column, and an essentially water-free mixture of polyoxymethylene dimethyl ethers having values of n greater than 1 which mixture is withdrawn from the distillation column near its bottom. A source of methanol can be admixed with the feedstream, and/or into the stages of contact with the acidic catalyst.

Suitable acidic catalysts include at least one member of the group consisting of bentonites, montmorillonites, cation-exchange resins, and sulfonated fluoroalkylene resin derivatives, preferably comprises a sulfonated tetrafluoroethylene resin derivative. A preferred class of acidic catalysts comprises at least one cation-exchange resin of the group consisting of styrene-divinylbenzene copolymers, acrylic acid-divinylbenzene copolymers, and methacrylic acid-divinylbenzene copolymers. Preferably, the heating of the bottom stream with the acidic catalyst employs at least one distillation column with internal and/or external stages of contact with the acidic catalyst.

Preferably, the heating of the bottom stream with the acidic catalyst employs at least one catalytic distillation column with internal and/or external stages of contact with the acidic catalyst, and internal zones to separate the methylal from the higher polyoxymethylene dimethyl ethers.

Suitable acidic catalysts include at least one member of the group consisting of bentonites, montmorillonites, cation-exchange resins, and sulfonated fluoroalkylene resin derivatives, preferably comprises a sulfonated tetrafluoroethylene resin derivative. A preferred class of acidic catalysts comprises at least one cation-exchange resin of the group consisting of styrene-divinylbenzene copolymers, acrylic acid-divinylbenzene copolymers, and methacrylic acid-divinylbenzene copolymers. Preferably, the heating of the bottom stream with the acidic catalyst employs at least one distillation column with internal and/or external stages of contact with the acidic catalyst.

Advantageously, the mixture of polyoxymethylene dimethyl ethers is contacted with an anion exchange resin to form an essentially acid-free mixture. Contacting with the anion exchange resin is preferably carried out within a section of the catalytic distillation column below the stages of contact with the acidic catalyst to form an essentially acid-free mixture.

In a preferred embodiment of the invention the essentially acid-free mixture of polyoxymethylene dimethyl ethers is fractionated within a section of the distillation column below the stages of contact with the acidic catalyst to provide an aqueous side-stream which is withdrawn from the distillation column, and an essentially water-free mixture of higher molecular weight polyoxymethylene dimethyl ethers (values of n greater 1) which is withdrawn from the distillation column near its bottom. Advantageously, at least a portion of the aqueous side-stream is used for recovery of an aqueous formaldehyde solution in an adsorption column.

Another aspect this invention is an integrated process which further comprises formation of the feedstream by a process comprising continuously contacting a gaseous feedstream comprising dimethyl ether, dioxygen and diluent gas with a catalytically effective amount of an oxidative dehydrogenation promoting catalyst comprising silver as an essential catalyst component at elevated temperatures to form a gaseous mixture comprising formaldehyde, methanol, dioxygen, diluent gas, carbon dioxide and water vapor; cooling the gaseous dehydrogenation mixture with an adsorption liquid and adsorbing formaldehyde therein; and separating the resulting liquid source of formaldehyde from a mixture of gases comprising dioxygen, diluent, carbon monoxide, carbon dioxide and water vapor.

At least a portion of the mixture of gases separated from the resulting aqueous source of formaldehyde is recycled into the gaseous feedstream.

Preferably the formaldehyde formed is recovered as an aqueous solution containing less than about 60 percent water, preferably less than about 50 percent water and more preferably less than about 25 percent water by using at least one continuous adsorption column with cooling to temperatures in a range downward from about 100° C. to 25° C.

Suitable sources of dioxygen are air or a dioxygen-enriched gas stream obtained by physically separating a gaseous mixture containing at least about 10 volume percent dioxygen into a dioxygen-depleted stream and a dioxygen-enriched gas stream. Preferably the gaseous mixture contains at least 60 volume percent dinitrogen and wherein the dioxygen-enriched gas stream comprises a volume ratio of dinitrogen to dioxygen of less than 2.5 to 1.

For this aspect of the invention, suitable oxidative dehydrogenation promoting catalyst comprises silver and optionally up to about 8 percent by weight of a compound selected from the group consisting of oxides of boron, phosphorous, vanadium, selenium, molybdenum and bismuth, phosphoric acid, ammonium phosphate and ammonium chloride.

For a more complete understanding of the present invention, reference should now be made to the embodiments illustrated in greater detail in the accompanying drawing and described below by way of examples of the invention.

GENERAL DESCRIPTION

The improved processes of the present invention employ a feedstream comprising methanol, formaldehyde and a soluble condensation promoting component capable of activating a heterogeneous acidic catalyst. Suitable components include any acidic compound soluble in the feedstream, preferably an organic compound soluble in a feedstream of about 30 to about 85 percent by weight formaldehyde in methanol solution containing less than 5 percent water.

A preferred class of condensation promoting components capable of activating a heterogeneous acidic catalyst includes members of the group consisting of low boiling, monobasic organic acids, more preferably acetic acid or formic acid.

In general, after the feedstream is heated with the heterogeneous catalyst it will contain a mixture of organic oxygenates at least one of which is of higher molecular weight than the starting formaldehyde and methanol. For example, effluent mixtures can comprise water, methanol, formaldehyde, methylal and other polyoxymethylene dimethyl ethers having a structure represented by the type formula $$CH_3O(CH_2O)_nCH_3$$

in which formula n is a number ranging between 12 and about 15, preferably between 1 and about 10. More preferably the mixture contains a plurality of polyoxymethylene dimethyl ethers having values of n are in a range from 2 to about 7. Conditions of reaction include temperatures in a range from about 50° to about 300° C., preferably in a range from about 150° to about 250° C.

Stoichiometry of this condensation may be expressed by the following equations;

$$CH_3OCH_3 + n\ CH_2O \rightarrow CH_3O(CH_2O)_nCH_3$$

$$2\ CH_3OH + m\ CH_2O \rightarrow CH_3O(CH_2O)_mCH_3 + H_2O$$

which may be combined as in the following equation when n is equal to m;

$$CH_3OCH_3 + 2\ CH_3OH + 2nCH_2O \rightarrow 2\ CH_3O(CH_2O)_nCH_3 + H_2O$$

As shown above, the synthesis of methylal and higher polyoxymethylene dimethyl ethers from dimethyl ether, methanol, and formaldehyde is a reversible reaction that yields water as a co-product. Under certain conditions at least a portion of the water may be consumed in a dehydrogenation reaction expressed by the following equations;

$$CH_3OCH_3 + CH_3OH + H_2O \rightarrow 3\ CH_2O + 3\ H_2$$

and $$CH_3OCH_3 + H_2O \leftarrow \rightarrow 2\ CH_3OH$$

Sources of dimethyl ether useful herein are predominantly dimethyl ether, preferably at least about 80 percent dimethyl ether by weight, and more preferably about 90 percent dimethyl ether by weight. Suitable dimethyl ether sources may contain other oxygen containing compounds such as alkanol and/or water, preferably not more than about 20 percent methanol and/or water by weight, and more preferably not more than about 15 percent methanol and/or water by weight.

The process can be performed at any temperature and pressure at which the reaction proceeds. Preferred temperatures are between about 20° and about 150° C., with between about 90° and about 125° C. being more preferred. The most preferred temperatures are between about 115° and about 125° C.

According to the present invention, the ratio of formaldehyde to dimethyl ether in the feedstreams is any mole ratio which results in the production of the desired oxygenated organic compound. The ratio of formaldehyde to dimethyl ether is preferably between about 10:1 and about 1:10 moles. The ratio of formaldehyde to dimethyl ether is preferable between about 5:1 and about 1:5 moles. More preferably, the ratio of formaldehyde to dimethyl ether is between about 2:1 and about 1:2 moles.

The process can be performed at any temperature and pressure at which the reaction proceeds. Preferred temperatures are between about 20° and about 150° C., with between about 90° and about 125° C. being more preferred. The most preferred temperatures are between about 115° and about 125° C.

The pressure can be atmospheric or super-atmospheric pressure. Preferred pressures are, according to the present invention, between about 1 and about 100 atmospheres, with between about 15 and about 25 atmospheres being most preferred.

The reaction mixture feed gas flow rate, expressed as gas hourly space velocity, can be between about 50 and about 50,000 $hr^{-1}$, most preferably, between about 100 and about 2,000 $hr^{-1}$. Un-converted dimethyl ether can be recovered from the mixture by methods well known in the art. One particularly desirable method is the use of distillation of the condensed product.

The process of this invention can be performed in either a fixed or fluid bed reactor, using either continuous or batch processing methods. It is preferred to use a fixed bed reactor and a continuous mode of operation.

The feed stream is heated in a catalytic distillation column with an acidic catalyst, which is heterogeneous to the feedstream, under conditions of reaction sufficient to convert formaldehyde and methanol present to methylal and higher polyoxymethylene dimethyl ethers. Examples of the solid acidic catalyst for use in the present invention include cation exchange resins, sulfonated fluoroalkylene resin derivatives, and crystalline aluminosilicates.

Cation exchange resins that can be used in the present invention may be carboxylated or sulfonated derivatives, but sulfonated derivatives are preferred because of the high reaction yield that can be attained. Ion exchange resins that can be used may be gel-type cation exchange resins or macroporous (macroreticular) cation-exchange resins, but the latter as exemplified by Amberlite 200C of Organc Co, Ltd. and Lewalit SP112 of Bayer A. G. are preferred because of the high reaction yield that can be attained. Specific examples of useful ion exchange resins include a styrene-divinylbenzene copolymer, an acrylic acid-divinylbenzene copolymer, a methacrylic acid-divinylbenzene copolymer, etc.

A sulfonated tetrafluoroethylene resin derivative (trade name, Naflon H) is preferably used as a sulfonated fluoroalkylene resin derivative.

The most desirable of these solid acidic catalysts are macroreticular cation exchange resins having sulfonate groups.

According to an integrated process of the invention a source of formaldehyde is formed by subjecting dimethyl ether in the vapor phase to oxidative dehydrogenation in the presence of a catalytically effective amount of an oxidative dehydrogenation promoting catalyst comprising silver as an essential catalyst component at elevated temperatures to form a gaseous mixture comprising formaldehyde, methanol, dioxygen, diluent gas, carbon monoxide, carbon dioxide and water vapor; cooling the gaseous dehydrogenation mixture with an adsorption liquid and adsorbing formaldehyde therein; and separating the resulting liquid source of formaldehyde from a mixture of gases comprising dioxygen, diluent, carbon monoxide, carbon dioxide and water vapor.

According to this aspect of the present invention, the ratio of dioxygen to total dimethyl ether is any mole ratio which results in the production of the desired source of formaldehyde. The ratio of dioxygen to total ether and, if present, alkanol is preferably between about 1:1 and about 1:1000 moles. More preferably, the ratio of dioxygen to dimethyl ether is between about 1:1 and about 1:100 moles. Most preferably, the ratio of dioxygen to dimethyl ether is between about 1:1 and about 1:10 moles.

Operating conditions of reaction usually fall in the following ranges: Dimethyl ether: 1 mol percent up to 17.4 mol percent.

Air: 99 mol percent to 82.6 mol percent

Reaction temperature: 200° to 450° C.

Space velocity: 1,000–20,000 $hr^{-1}$

Preferable conditions are as follows:

Dimethyl ether: 3 mol percent to 12 mol percent

Reaction temperature: 250° to 400° C.

Space velocity: 1,000–10,000 $hr^{-1}$

The dioxygen can be added to the reaction mixture as pure molecular oxygen, or diluted with an inert gas such as nitrogen or argon. It is preferred to keep the dioxygen at no more than 10 mole percent of the entire reaction feed so as to avoid the formation of explosive mixtures.

The Karl Fischer process, developed in the early 1900s by Karl Fischer Apparate and Rohrleitungsbau of Germany, is probably the most widely used silver catalyst process.

Several features distinguish this type of process from those catalyzed by metal oxides. Whereas the metal oxide processes achieve an overall yield of about 93 percent, commercial silver catalyzed units are generally believed to achieve an overall yield of about 88 percent. Per-pass methanol conversion is about 80 percent, with 90 percent selectivity to formaldehyde. The silver-catalyzed process operates with an excess of methanol and requires a specialized piece of equipment, such as a packed tower or a methanol boiler equipped with a special air mixer, to generate the methanol-air feed mixture. Since less air is used, however, equipment sizes are smaller and power consumption is less than for the metal oxide process.

The silver-catalyzed reaction is endothermic; but depending on the amount of feed preheat and air added, the exothermic reaction of oxygen with hydrogen sustains the reaction at temperatures in excess of 550° C. Steam can then be generated by cooling the reactor effluent before it is fed to the absorber. However, the steam has a lower pressure (about 30 psig), and the amount produced is insufficient to satisfy process steam requirements. This steam deficit is offset by the fuel value of the substantial amount of hydrogen (more than 18 vol percent) that remains in the absorber off-gas. If the absorber off-gas is processed in a thermal oxidizer, a blower for additional combustion air is required, but a substantial amount of 200 psig steam may be produced.

The dioxygen can be added to the reaction mixture as pure molecular oxygen, or diluted with an inert gas such as nitrogen or argon. It is preferred to keep the dioxygen at no more than 10 mole percent of the entire reaction feed so as to avoid the formation of explosive mixtures.

According to the present invention, within the oxidation reaction zone dimethyl ether is oxidized with a source of dioxygen in the presence of an oxy-dehydrogenation catalytic composition containing, as an essential ingredient, silver with or without up to about 10 percent of a supplemental inorganic compound based upon the total weight of metal oxide and supplemental inorganic compounds. Suitable oxy-dehydrogenation catalysts have been developed for converting methanol with a source of dioxygen to produce formaldehyde, as described in U.S. Pat. No. 5,401,884, U.S. Pat. No. 5,102,838, U.S. Pat. No. 4,786,743, U.S. Pat. No. 4,521,618, U.S. Pat. No. 4,474,996 and U.S. Pat. No. 4,359,587 which patents are specifically incorporated herein in their entirety by reference.

The starting materials are fed through a silver-containing fixed-bed catalyst installed in a vertical tubular reactor. The catalyst preferably comprises silver crystals having a particle size of from 0.1 to 3 mm, in particular from 0.2 to 2.5 mm. The fixed-bed catalyst can have a multi-layer structure through arrangement of the silver crystals in layers of different particle size.

The starting mixture of dimethyl ehter vapor, oxygen-containing gas, and, if used, steam and inert gas is preferably passed through the tubular reactor from top to bottom.

Otherwise, the process is carried out in one step by passing the starting mixture through the fixed catalyst bed at from 550° to 750° C., in particular from 600° to 720° C., particularly advantageously at from 660° to 700° C. The process is preferably carried out continuously at from 0.5 to 3 bar, in particular at from 0.8 to 2 bar, preferably at from 1 to 1.5 bar. The residence times in the catalyst zone are from 0.001 to 1 second, preferably from 0.002 to 0.1 second. The reaction gases leaving the catalyst zone are advantageously cooled within a short time, for example to below 350° C. The cooled gas mixture can expediently be fed to an adsorption tower, in which the formaldehyde is washed out of the gas mixture by means of water.

In the present method, dimethyl ether may be used alone, or methanol and dimethyl ether can be used in admixture with each other to produce formaldehyde.

DESCRIPTION OF THE PREFERRED EMBODIMENTS

Figure 1:
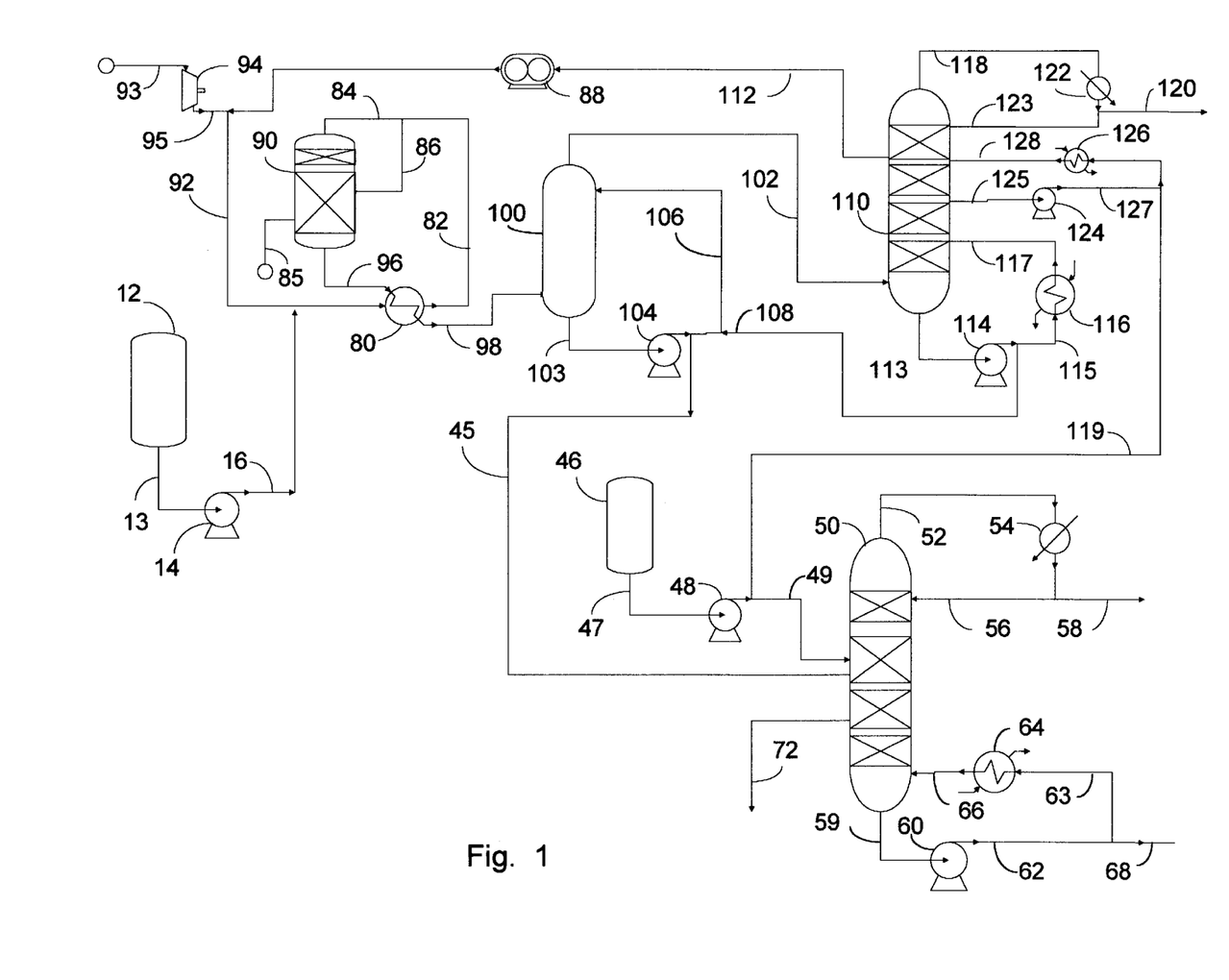
FIG. 1 is a schematic flow diagram depicting a preferred aspect of the present invention for continuous catalytic production of polyoxymethylene dimethyl ethers by chemical conversion of methanol and formaldehyde in which a feedstream comprising a soluble condensation promoting component capable of activating a heterogeneous acidic catalyst is heated with the heterogeneous acidic catalyst in a catalytic distillation column with internal stages of contact. A liquid portion of the effluent of condensation, containing polyoxymethylene dimethyl ethers, is contacted with an anion exchange resin disposed within a section of the distillation column below the stages of contact with the acidic catalyst to form an essentially acid-free mixture, and fractionated to provide suitable components for blending into diesel fuel. The feedstream in the integrated process depicted in FIG. 1 is a stream of aqueous formaldehyde in methanol derived from oxidative dehydrogenation of dimethyl ether. In this aspect of invention, recycle gas from the formaldehyde absorber is combined with air, mixed with dimethyl ether, preheated against reactor product, and then fed to the formaldehyde reactor.

In order to better communicate the present invention, still another preferred aspect of the invention is depicted schematically in FIG. 1. In this integrated process a feedstream comprising methanol, formaldehyde and a soluble condensation promoting component capable of activating a heterogeneous acidic catalyst is provided by contacting dimethyl ether in the vapor phase with a catalytically effective amount of an oxidative dehydrogenation promoting catalyst comprising silver as an essential catalyst component at elevated temperatures to form a gaseous mixture comprising formaldehyde, methanol, dioxygen, diluent gas, carbon dioxide and water vapor; cooling the gaseous dehydrogenation mixture with an adsorption liquid and adsorbing formaldehyde therein; and separating the resulting liquid source of formaldehyde from a mixture of gases comprising dioxygen, diluent, carbon monoxide, carbon dioxide and water vapor. In this aspect of invention, recycle gas from the formaldehyde absorber is combined with air, mixed with dimethyl ether, preheated against reactor product, and then fed to the formaldehyde reactor.

Referring now to the upper portion of FIG. 1, a mixture containing dimethyl ether in substantially liquid form is supplied from dimethyl ether storage vessel 12 to pump 14 through conduit 13. Dimethyl ether is transferred through conduit 16 into feed manifold 92. A recycle stream of wet gas is transferred into feed manifold 92 by means of blower 88. A gaseous stream containing dioxygen and dinitrogen from a source (not shown) is supplied to compressor 94 through conduit 93. Compressed gas is transferred through conduit 95, combined in feed manifold 92 with the recycle stream of wet gas from the formaldehyde adsorber and the dimethyl ether. The resulting mixture is heated against reactor effluent in heat exchanger 80, and transferred into oxidation reactor 90 through conduit 82 and feed manifold 84.

Formaldehyde reactor 90 contains an oxidative dehydrogenation catalyst disposed in a thin layer directly above a vertical heat exchanger where effluent from the catalyst layer is promptly cooled. Boiler feed water at about 110° to 130° C. is supplied through conduit 85 to the heat exchanger for generation of low pressure steam in the lower section of the formaldehyde reactor. The steam is transferred through conduit 86, mixed with the preheated mixture of dimethyl ether, wet recycle gas and air stream in feed manifold 84, and transferred into formaldehyde reactor 90. Steam is metered into the preheated methanol-air mixture to control the reactor outlet temperature. The mole ratio of fresh air feed to methanol is between 0.5 and 2.0, preferably about 1.25 and typically the mole ratio of dimethyl ether to steam is about 3. The pressure is only slightly above atmospheric. Since the catalyst layers are less than one inch in thickness, the pressure drop is negligible.

In this embodiment of the invention, metallic silver catalyzes the conversion of dimethyl ether to formaldehyde by a reversible dehydrogenation reaction at temperatures from about 500° to 700° C:

$$CH_3OCH_3 + \tfrac{1}{2} O_2 \rightarrow 2CH_2O + H_2$$

The oxidative dehydrogenation catalyst is generally silver crystals supported on a stainless steel mesh, or a shallow bed of silver crystals, spherical particles, or granules. The reaction is endothermic, and theoretical equilibrium is approximately 50 percent yield at 400° C., 90 percent at 500° C., and 99 percent at 700° C. To conveniently sustain elevated reaction temperatures required to obtain high yields, a portion of the hydrogen formed is oxidized to water. Formation of water is exothermic and provides heat to maintain the endothermic hydrogenation reaction. Heat is also provided by the direct oxidation of methanol:

$$CH_3OH + \tfrac{1}{2} O_2 \rightarrow CH_2O + H_2O$$

These reactions are rapid and therefore the process is essentially adiabatic. At 650° C., the reaction is substantially complete with contact times of less than 0.01 second. Methanol conversion in the reactor is typically between 65 percent and 80 percent, depending largely on the amount of steam introduced at the methanol vaporization step. Formaldehyde is lost by several side reactions, including those producing co-products including carbon monoxide, carbon dioxide, methane, formic acid, and methyl formate.

To minimize side reactions, it is important to avoid excess oxygen and to operate with exposure time of products and reactants to the catalyst at high temperatures as short as possible. An excess of methanol or methanol and steam is also important, serving to avoid an explosive feed composition. A mixture containing between 6.7 mol percent and 36.5 mol percent methanol in air at 1 atm constitutes a severe explosion hazard.

Gaseous effluent from oxidation reactor 90 is transferred through conduit 96, cooled against the reactor feedstream in exchanger 80 and then passed to an absorption system, where aqueous formaldehyde is absorbed in methanol. The effluent gases flow through conduit 98 into spray column 100 where a solution of formaldehyde is formed. Formaldehyde solution from the bottom of spray column 100, at temperatures in a range downward from about 100° C. to about 75° C., is supplied to pump 104 through conduit 103. A portion of the aqueous formaldehyde is transferred through conduit 45 into reactive distillation column 50. Formaldehyde solution from the spray column is generally about 55 percent by weight formaldehyde, about 43 methanol weight percent about 2 weight percent water and less than 350 ppm of formic acid.

It should be apparent that effluent from the spray column is a valuable product in itself A portion of the stream can optionally be diverted from adsorption tower 100 for delivery to a destination (not shown) where the stream may subsequently be separated to recover, for example, formaldehyde and methanol and/or dimethyl ether. The stream can alternatively be utilized as a source of feed stock for chemical manufacturing.

Formaldehyde solution is combined with a solution of formaldehyde supplied from the bottom of adsorption column 110 through conduits 113 and 108, by means of pump 114, and circulated to the top of spray column 100 through conduit 106. It is important to maintain the temperature of the pump-around stream above about 70° C. to prevent paraformaldehyde formation. Optionally, a portion of the cooling required in spray column 100 may be obtained by including a heat exchanger in the flow through conduit 106.

A gaseous overhead stream from spray column 100 is transferred through conduit 102 into adsorption column 110, which contains a high efficiency packing or other means for contacting counter-currently the gaseous stream with aqueous adsorption liquid. A dilute aqueous formaldehyde from the bottom of adsorption column 110 is circulated in a pump-around to the bottom section of the column through conduits 113 and 115, cooler 116, and conduit 117 by means of pump 114.

Further up the column pump-arounds are be cooled to successively lower temperatures. In this embodiment of the invention a liquid side stream is supplied to pump 124 through conduit 125, transferred through manifold 127, cooled in cooler 126, and returned to adsorption column 110 through conduit 128.

In some configurations, the lower pump-around stream is not cooled at all. Caustic solution may be added to the chilled water to improve absorber performance, but it leaves traces of sodium as a contaminant in the product.

A vapor side draw from adsorption column 110 is transferred through conduit 112 and mixed with fresh air as previously described.

The adsorber overhead passes through conduit 118 into condenser 122. An appropriate amount of condensate is formed and refluxed to the top section of the adsorber column through conduit 123. Overhead temperatures in adsorption column 110 are in a range of about 15° to about 55° C., preferably about 30° to about 40° C. Gases are vented from condenser 122 through conduit 120 to disposal, typically, in a thermal oxidation unit (not shown).

The absorber overhead, which contains trace amounts of formaldehyde (about 10–30 ppm), is treated in several ways by catalytic or thermal converter to oxidize hydrocarbons and recuperative heat exchange. Typically, 170 psig to 200 psig steam is generated to improve overall economics of preferred embodiments of the invention.

A portion of the solution of formaldehyde in methanol is diverted from pump 104 into reactive distillation column 50 through conduit 45. In reactive distillation column 50 simultaneous chemical reaction and multicomponent distillation are carried out coextensively in the same high efficiency, continuous separation apparatus. Optionally, a stream containing methanol from storage vessel 46 may by fed into the reactive distillation column 50. Charge pump 48 transfers methanol in substantially liquid form into the reactive distillation column 50 through conduits 47 and 49.

Solid acidic catalyst is present in the reactive distillation column 50 to allow solutions containing water, methanol, formaldehyde, methylal and one or more other polyoxymethylene dimethyl ethers to be brought into solid-liquid contact counter-currently with the catalyst to form products including methylal and higher molecular weight polyoxymethylene dimethyl ethers. More volatile reaction products are taken overhead from the high efficiency separation apparatus, whereas water and less volatile reaction products are carried down the high efficiency separation apparatus.

The overhead vapor stream from reactive distillation column 50 is transferred through conduit 52 into condenser 54. A suitable portion of condensate from condenser 54 is refluxed into reactive distillation column 50 through conduit 56. A product stream containing methylal is transferred through conduit 58 to product storage (not shown). Conduit 59 supplies pump 60 with liquid containing higher molecular weight polyoxymethylene dimethyl ethers from the bottom of column 50. A suitable portion of liquid from the bottom of column 50 is transferred, by means of pump 60, through conduits 62 and 63 into reboiler 64 which is in flow communication with the bottom of the column by means of conduit 66. A product stream containing higher molecular weight polyoxymethylene dimethyl ethers is transferred through conduit 68 to product storage (not shown). Preferably, an anion exchange resin is disposed within a section of the distillation column below the stages of contact with the acidic catalyst to form an essentially acid-free mixture.

An aqueous side stream containing low levels of unreacted formaldehyde and/or methanol is discharged from column 50 through conduit 72.

In view of the features and advantages of the continuous catalytic processes for direct condensation of formaldehyde and dimethyl ether to form a mixture containing one or more polyoxymethylene dimethyl ethers in accordance with this invention, as compared to the known methanol condensation systems previously used, the following examples are given.

EXAMPLE 1

Products of several condensation runs were composited, and the composite vacuum filtered through a medium glass frit. A 90 gram aliquot of filtrate was shaken with 20 grams of basic ion-exchange resin beads (DOWEX 66) which were then allowed to settle for one hour. The resulting supernatant liquid was then gravity filtered through a medium paper filter. A suitable amount (54 grams) of molecular sieve type 3A, which had been activated by calcination at about 538° C., was mixed into the filtrate, and the mixture allowed to stand overnight at ambient temperatures. Liquid was separated from the sieve by vacuum filtration through a medium glass frit. A 45.97 gram aliquot of this acid-free, dry filtrate was charged to a small distillation apparatus consisting of a 100 mL 3-neck flask, a fractionating column and condenser. The charge was distilled into eight overhead fractions which were collected at temperature cuts according to the following schedule.

| Fraction | Temperatures, ° C. | |
|---|---|---|
| Number | Overhead | Bottom |
| 1 | 42 to 46 | 70 to 94 |
| 2 | 47 to 76 | 95 to 109 |
| 3 | 77 to 94 | 110 to 118 |
| 4 | 95 to 100 | 119 to 127 |
| 5 | 101 to 107 | 128 to 136 |
| 6 | 108 to 112 | 137 to 146 |
| 7 | 113 to 123 | 147 to 162 |
| 8 | 124 to 150 | 163 to 174 |

White solids (possibly paraformaldehyde) were observed in the column and condenser during cuts 2 through 4, but not thereafter. Composition of the distilled fraction and bottoms are given in Table I.

source of formaldehyde by nonoxidative dehydrogenation of dimethyl ether and steam. The liquid feed of water was fed by a syringe pump into the preheat zone above the catalyst bed. Using mass flow controllers, a gaseous feedstream of 89.1 percent by volume dimethyl ether and 10.9 volume percent nitrogen was also fed to the top of the reactor. Samples were collected while temperature of the catalyst bed was controlled to temperatures in a range from about 400° to about 650° C. Operating conditions and results are summarized in Table III For the purposes of the present invention, "predominantly" is defined as more than about fifty percent. "Substantially" is defined as occurring with sufficient frequency or being present in such proportions as to measurably affect macroscopic properties of an associated compound or system. Where the frequency or proportion for such impact is not clear, substantially is to be regarded as about twenty per cent or more. The term "essentially" is defined as absolutely except that small variations which have no more than a negligible effect on macroscopic qualities and final outcome are permitted, typically up to about one percent.

TABLE I

COMPOSITION OF OVERHEAD FRACTIONS AND BOTTOMS

| | Compound | | | | $CH_3O(CH_2O)_nCH_3$ where the value of n is: | | | | | |
|---|---|---|---|---|---|---|---|---|---|---|
| Fraction | Methylal | Methanol | Hemiacetals | Trioxane | 2 | 3 | 4 | 5 | 6 | 7 |
| Starting | 49.95 | 0.0 | 0.69 | 2.42 | 22.60 | 12.42 | 6.40 | 3.15 | 1.45 | 0.61 |
| 1 | 97.21 | 0.95 | 0.05 | 0.0 | 0.46 | 0 | 0 | 0 | 0 | 0 |
| 2 | 93.83 | 2.52 | 0.38 | 0.0 | 2.84 | 0 | 0 | 0 | 0 | 0 |
| 3 | 20.81 | 12.92 | 8.85 | 2.39 | 54.80 | 0.17 | 0 | 0 | 0 | 0 |
| 4 | 3.24 | 11.12 | 6.40 | 4.49 | 74.19 | 0.57 | 0 | 0 | 0 | 0 |
| 5 | 0.56 | 8.47 | 2.29 | 5.83 | 82.07 | 0.78 | 0 | 0 | 0 | 0 |
| 6 | 0.40 | 3.10 | 0.16 | 7.21 | 88.05 | 1.08 | 0 | 0 | 0 | 0 |
| 7 | 0.43 | 0.99 | 0.0 | 9.38 | 86.60 | 2.55 | 0.05 | 0 | 0 | 0 |
| 8 | 0.32 | 0.47 | 0.0 | 11.77 | 82.98 | 4.37 | 0.08 | 0 | 0 | 0 |
| Bottoms | 0.29 | 0.02 | 0.0 | 0.54 | 1.10 | 49.49 | 26.19 | 13.05 | 6.34 | 2.96 |

EXAMPLE 2

In this Example a silver catalyst in the form of needles was used at several elevated temperatures to provide a source of formaldehyde by oxidative dehydrogenation of dimethyl ether, steam and methanol. A tubular quartz reactor was charged with 3.83 grams (1 cc) of the silver needles. The tubular quartz reactor (approx. 10 mm inside diameter) was equipped with a quartz thermowell terminating at about the midpoint of the catalyst bed. Quartz wool was placed above the catalyst zone to assist in vaporizing liquid feed. The liquid feed solution containing 18.6 percent methanol and 81.4 percent by weight water was fed by a syringe pump into the preheat zone above the catalyst bed. Using mass flow controllers, a gaseous feedstream of 59.93 percent by volume dimethyl ether, 31.59 volume percent nitrogen and 8.48 percent by volume dioxygen was also fed to the top of the reactor. Samples were collected while temperature of the catalyst bed was controlled to temperatures in a range from about 400° to about 650° C. Operating conditions and results are summarized in Table II.

EXAMPLE 3

In this Example a silver catalyst in the form of needles was used at several elevated temperatures to provide a

TABLE II

| Oxidative Dehydrogenation of Dimethyl Ether Using a Catalyst of Silver Needles | | |
|---|---|---|
| Temperature, ° C. | 397 | 508 |
| Run Time, min | 60 | 100 |
| Gas Feed, mol percent | | |
| Nitrogen | 31.59 | 31.69 |
| DME | 59.93 | 59.93 |
| Dioxygen | 8.48 | 8.48 |
| Liquid Feed, weight percent | | |
| Methanol | 18.6 | 18.6 |
| Water | 81.4 | 81.4 |
| Feed Rates | | |
| Gas scc/min | 146 | 146 |
| Liquid mL/min | 0.4125 | 0.4125 |
| Conversions, mole percent | | |
| Methanol | 9.21 | 10.55 |
| DME | 15.44 | 16.41 |
| Net MeO | 14.01 | 15.08 |
| Dioxygen | 94.40 | 93.85 |

TABLE II-continued

Oxidative Dehydrogenation of Dimethyl Ether
Using a Catalyst of Silver Needles

| Selectivities, percent | | |
|---|---|---|
| Light Alkanes | 1.37 | 4.07 |
| CO | 18.19 | 20.15 |
| $CO_2$ | 9.06 | 7.92 |
| Formaldehyde | 56.57 | 59.16 |
| Methylal | 0 | 0 |
| HPE | 0 | 0 |
| DME/Methanol | 3.23 | 3.20 |
| Temperature, ° C. | 614 | 660 |
| Run Time, min | 150 | 195 |
| Gas Feed, mol percent | | |
| Nitrogen | 31.59 | 31.69 |
| DME | 59.93 | 59.93 |
| Dioxygen | 8.48 | 8.48 |
| Liquid Feed, weight percent | | |
| Methanol | 18.6 | 18.6 |
| Water | 81.4 | 81.4 |
| Feed Rates | | |
| Gas scc/min | 146 | 146 |
| Liquid mL/min | 0.4125 | 0.4125 |
| Conversions, mole percent | | |
| Methanol | 13.53 | 15.30 |
| DME | 17.18 | 23.94 |
| Net MeO | 16.34 | 21.96 |
| Dioxygen | 94.28 | 94.53 |
| Selectivities, percent | | |
| Light Alkanes | 19.47 | 28.59 |
| CO | 25.41 | 20.15 |
| $CO_2$ | 5.29 | 3.39 |
| Formaldehyde | 45.79 | 37.70 |
| Methylal | 0 | 0 |
| HPE | 0 | 0 |
| DME/Methanol | 3.30 | 3.10 |

Where HPE is higher polyoxymethylene dimethyl ethers which are $CH_3O(CH_2O)_nCH_3$ having n greater than 1, MeO is methoxy moiety, and DME is dimethyl ether.

TABLE III

Nonoxidative Dehydrogenation of Dimethyl Ether
Using a Catalyst of Silver Needles

| Temperature, ° C. | 408 | 511 |
|---|---|---|
| Run Time, min | 115 | 175 |
| Gas Feed, mol percent | | |
| Nitrogen | 10.9 | 10.9 |
| DME | 89.1 | 89.1 |
| Liquid Feed, weight percent | | |
| Water | 100 | 100 |
| Feed Rates | | |
| Gas scc/min | 102 | 102 |
| Liquid mL/min | 0.07563 | 0.07563 |
| Conversions, mole percent | | |
| DME | 3.63 | 2.56 |
| Net MeO | 3.63 | 2.56 |
| Selectivities, percent | | |
| Light Alkanes | 46.21 | 46.48 |
| CO | 0 | 0 |
| $CO_2$ | 0 | 0 |
| Formaldehyde | 53.79 | 53.52 |
| Methylal | 0 | 0 |
| HPE | 0 | 0 |

TABLE III-continued

Nonoxidative Dehydrogenation of Dimethyl Ether
Using a Catalyst of Silver Needles

| Temperature, ° C. | 612 | 650 |
|---|---|---|
| Run Time, min | 290 | 465 |
| Gas Feed, mol percent | | |
| Nitrogen | 10.9 | 10.9 |
| DME | 89.1 | 89.1 |
| Liquid Feed, weight percent | | |
| Water | 100 | 100 |
| Feed Rates | | |
| Gas scc/min | 102 | 102 |
| Liquid mL/min | 0.07563 | 0.07563 |
| Conversions, mole percent | | |
| DME | 9.38 | 23.39 |
| Net MeO | 9.36 | 23.28 |
| Selectivities, percent | | |
| Light Alkanes | 53.06 | 52.51 |
| CO | 5.51 | 14.96 |
| $CO_2$ | 0.34 | 0.25 |
| Formaldehyde | 41.10 | 32.29 |
| Methylal | 0 | 0 |
| HPE | 0 | 0 |

Where HPE is higher polyoxymethylene dimethyl ethers which are $CH_3O(CH_2O)_nCH_3$ having n greater than 1, MeO is methoxy moiety and DME is dimethyl ether.

That which is claimed is:

1. A process for the catalytic production of a mixture of oxygenated organic compounds suitable as a blending component of fuel for use in compression ignition internal combustion engines, which process comprises providing a feedstream comprising a soluble condensation promoting component capable of activating a heterogeneous acidic catalyst and a source of formaldehyde formed by conversion of dimethyl ether in the presence of a catalyst comprising silver as an essential catalyst component; and heating the feedstream with the heterogeneous acidic catalyst under conditions of reaction sufficient to form an effluent of condensation comprising water, methanol, and methylal and one or more polyoxymethylene dimethyl ethers having a structure represented by the formula $$CH_3O(CH_2O)_nCH_3$$

where n is a number from 1 to about 10.

2. The process according to claim 1 wherein the soluble condensation promoting component capable of activating the heterogeneous acidic catalyst comprises at least one member of the group consisting of formic and acetic acids.

3. The process according to claim 2 wherein the acidic catalyst comprises at least one member of the group consisting of bentonite, montmorillonite, cation exchange resins, and sulfonated fluoroalkylene resin derivatives.

4. The process according to claim 2 wherein the acidic catalyst comprises at least one cation exchange resin of the group consisting of styrene-divinylbenzene copolymers, acrylic acid-divinylbenzene copolymers, and methacrylic acid-divinylbenzene copolymers.

5. The process according to claim 2 wherein the acidic catalyst comprises a sulfonated tetrafluoroethylene resin derivative.

6. The process according to claim 1 wherein at least a liquid of the effluent containing polyoxymethylene dimethyl ethers is contacted with an anion exchange resin to form an essentially acid-free mixture.

7. The process according to claim 1 wherein the heating of the feedstream with the acidic catalyst is carried out at temperatures in a range from about 45° to about 90° C. and employs at least one catalytic distillation column having internal and/or external stages of contact with the acidic catalyst and internal zones to separate methylal from the polyoxymethylene dimethyl ethers.

8. The process according to claim 7 wherein at least a liquid portion of the effluent containing polyoxymethylene dimethyl ethers is contacted with an anion exchange resin disposed within a section of the distillation column below the stages of contact with the acidic catalyst to form an essentially acid-free mixture.

9. The process according to claim 8 wherein the essentially acid-free mixture of polyoxymethylene dimethyl ethers is fractionated within a section of the distillation column below the stages of contact with the acidic catalyst to provide an aqueous side-stream which is withdrawn from the distillation column, and an essentially water-free mixture of polyoxymethylene dimethyl ethers having values of n greater than 1 which mixture is withdrawn from the distillation column near its bottom.

10. The process according to claim 7 wherein a source of methanol is admixed with the feedstream, and/or into the stages of contact with the acidic catalyst.

11. The process according to claim 1 which further comprises formation of the feedstream by a process comprising continuously contacting a gaseous feedstream comprising dimethyl ether, dioxygen and diluent with a catalytically effective amount of an oxidative dehydrogenation promoting catalyst comprising silver as an essential catalyst component at elevated temperatures to form a gaseous mixture comprising formaldehyde, dimethyl ether, dioxygen, diluent, carbon monoxide, carbon dioxide and water vapor; cooling the gaseous oxidation mixture with an adsorption liquid and adsorbing formaldehyde therein; and separating the resulting liquid source of formaldehyde from a mixture of gases comprising dioxygen, diluent, carbon monoxide, carbon dioxide and water vapor.

12. The process according to claim 11 wherein the contacting of the gaseous feedstream with the oxidative dehydrogenation promoting catalyst is carried out at temperatures in a range from about 590° to about 620° C.

13. The process according to claim 11 wherein the oxidative dehydrogenation promoting catalyst comprises silver and optionally up to about 8 percent by weight of a compound selected from the group consisting of phosphoric acid, ammonium phosphate, ammonium chloride, and oxides of boron, phosphorous, vanadium, selenium, molybdenum and bismuth.

14. The process according to claim 11 wherein the source of dioxygen is air.

15. The process according to claim 11 wherein the formaldehyde formed is recovered as an aqueous solution containing less than 25 percent water by using at least one continuous adsorption column with cooling to temperatures in a range downward from about 100° C. to 25° C.

16. The process according to claim 11 wherein the source of dioxygen is a dioxygen enriched gas stream obtained by physically separating a gaseous mixture, containing at least about 10 volume percent dioxygen, into a dioxygen depleted stream and a dioxygen-enriched gas stream.

17. The process according to claim 16 wherein the gaseous mixture contains at least 60 volume percent dinitrogen, and wherein the dioxygen enriched gas stream comprises a volume ratio of dinitrogen to dioxygen of less than 2.5 to 1.

18. The process according to claim 16 wherein the gaseous mixture is air.

* * * * *

UNITED STATES PATENT AND TRADEMARK OFFICE
CERTIFICATE OF CORRECTION

PATENT NO. : 6,265,528 B1
DATED : July 24, 2001
INVENTOR(S) : Gary P. Hagen, Michael J. Spangler It is certified that error appears in the above-identified patent and that said Letters Patent is hereby corrected as shown below:

Column 1,
Line 60, "Scientist Jul. 3, 1986) 35." should read -- Scientist (Jul. 3, 1986) 35."

Column 4,
Line 62, and at a temperatures of" should read -- and at temperatures of --

Column 5,
Line 1, "molar ratio of about" should read -- a molar ratio of about --

Column 6,
Line 7, "acids, preferable the group" should read -- acids, preferably, the group --
Line 8, "More preferable soluble" should read -- More preferably, soluble --
Line 13, "carried out at in at least" should read -- carried out in at least --
Line 52, derivatives, preferably comprises" should read -- derivatives, which preferably comprises --

Column 7,
Line 8, "of n greater 1)" should read -- of n greater than 1) --
Line 11, "in an adsorption column." should read -- in an absorber. --
Line 12, "aspect this invention is an" should read -- aspect of this invention is an --.
Lines 21 and 22, "with an adsorption liquid and adsorbing formaldehyde" should read -- with liquid and collecting formaldehyde --
Line 33, "continuous adsorption column with cooling" should read -- continuous absorber with cooling --

Column 8,
Line 6, "this aspect of invention," should read -- this aspect of the invention, --
Lines 36 and 37, "between 12 and about 15," should read -- between 1 and about 15, --
Line 39, "having values of n are in a range" should read -- having values of n which are in a range --
Line 44, "the following equations;" should read -- the following equations: --
Line 50, "n is equal to m;" should read -- n is equal to m: --
Line 59, "the following equations," should read -- the following equations: --

Column 9,
Lines 18 and 19, "ether is preferable between" should read -- ether is preferably between --
Line 44, "The feed stream is heated" should read -- The feedstream is heated --

Column 10,
Lines 13 and 14, "with an adsorption liquid and adsorbing formaldehyde" should read -- with liquid and collecting formaldehyde --

UNITED STATES PATENT AND TRADEMARK OFFICE
CERTIFICATE OF CORRECTION

PATENT NO. : 6,265,528 B1
DATED : July 24, 2001
INVENTOR(S) : Gary P. Hagen, Michael J. Spangler It is certified that error appears in the above-identified patent and that said Letters Patent is hereby corrected as shown below:

Column 11,
Line 31, "dimethyl ehter vapor," should read -- dimethyl ether vapor, --
Lines 44 and 45, "fed to an adsorption tower, in which" should read -- fed to an absorber, in which --
Lines 65 and 66, "with an adsorption liquid and adsorbing formaldehyde" should read -- with liquid and collecting formaldehyde --

Column 12,
Line 16, "the formaldehyde adsorber and" should read -- the formaldehyde absorber and --

Column 13,
Line 19, "weight percent about 2 weight" should read -- weight percent, about 2 weight --
Line 22, "product in itself A portion" should read -- product in itself. A portion"
Line 23, "from adsorption tower 100 for" should read -- from spray column 100 for --
Line 27, "source of feed stock for" should read -- source of feedstock for --
Lines 30 and 31, "the bottom of adsorption colum 110" should read -- the bottom of absorber 110 --
Line 39, "102 into adsorption column 110," should read -- 102 into absorber 110, --
Line 41 and 42, "with aqueous adsorption liquid." should read -- with aqueous liquid. --
Line 43, "the bottom of adsorption column 110" should read -- the bottom of absorber 110 --
Line 47, "pump-arounds are be cooled to" should read -- pump-arounds are to be cooled to --
Line 51, "returned to adsorption column 110" should read -- returned to absorber 110 --
Line 57, "draw from adsorption column 110" should read -- draw from absorber 110 --
Line 60, "The adsorber overhead passes" should read -- The absorber overhead passes --
Lines 62 and 63, "section of the adsorber column through" should read -- section of the absorber through --
Lines 63 and 64, "in adsorption column 110 are in" should read -- in absorber 110 are in --

Column 14,
Line 65, "and the mixture allowed to" should read -- and the mixture was allowed to --

Column 16,
Line 11, "in Table III" should read -- in Table III. --
Lines 20 and 21, "twenty per cent or more." should read -- twenty percent or more. --

UNITED STATES PATENT AND TRADEMARK OFFICE
CERTIFICATE OF CORRECTION

PATENT NO. : 6,265,528 B1
DATED : July 24, 2001
INVENTOR(S) : Gary P. Hagen, Michael J. Spangler It is certified that error appears in the above-identified patent and that said Letters Patent is hereby corrected as shown below:

Column 17,
Line 39, "$CH_3O(CH_2O)_uCH_3$" should read -- $CH_3O(CH_2O)_nCH_3$ --

Column 19,
Line 35, "with an adsorption liquid and adsorbing formaldehyde" should read -- with liquid and collecting formaldehyde --

Column 20,
Line 1, "with an adsorption liquid and adsorbing formaldehyde" should read -- with liquid and collecting formaldehyde --
Line 21, "continuous adsorption column with cooling" should read -- continuous absorber with cooling --

Signed and Sealed this

Twelfth Day of March, 2002

Attest:

Attesting Officer

JAMES E. ROGAN
Director of the United States Patent and Trademark Office